United States Patent [19]
Meyer, III

[11] Patent Number: 5,626,143
[45] Date of Patent: May 6, 1997

[54] PORTABLE CORDLESS CARDIOPULMONARY ARREST RECORDER AND METHOD

[76] Inventor: Magnus O. Meyer, III, 305 Berry Brook Ct., Ellisville, Mo. 63011

[21] Appl. No.: 372,037

[22] Filed: Jan. 12, 1995

[51] Int. Cl.$^6$ .................................................. A61B 5/0404
[52] U.S. Cl. ............................................................ 128/700
[58] Field of Search ................................. 128/670, 700, 128/711, 710, 697

[56] References Cited

U.S. PATENT DOCUMENTS

| | | |
|---|---|---|
| D. 253,609 | 12/1979 | Smith et al. ............. 128/711 |
| 4,211,238 | 7/1980 | Shu et al. ................ 128/700 |
| 4,457,312 | 7/1984 | Ornato et al. . |
| 4,532,934 | 8/1985 | Kelen ..................... 128/711 |
| 4,624,263 | 11/1986 | Slavin . |
| 4,993,420 | 2/1991 | Welkowitz . |
| 5,012,411 | 4/1991 | Policastro et al. . |
| 5,080,105 | 1/1992 | Thornton . |
| 5,213,107 | 5/1993 | Fujii . |
| 5,343,869 | 9/1994 | Pross et al. . |

Primary Examiner—William E. Kamm
Assistant Examiner—Scott M. Getzow
Attorney, Agent, or Firm—Robbins & Robbins

[57] ABSTRACT

A portable cordless cardiopulmonary arrest recorder is provided by this invention. The arrest recorder is used by the attending personnel at the treatment site for a cardiac-arrest patient. It has multiple chronometers for recording the time and duration of significant events and three sections for recording the patient's rhythm, medication and cardiovert/defibrillation. A visual screen and keyboard for typing additional data is provided. The recorder is designed to manually interface with a central processing unit to transfer data, and recharge the recorder. The recorder subsequently interfaces with a printer and allows for entry of additional information. Optionally the recorder may have provisions for receiving a conventional computer disk capable of storing data which may be interfaced with the central processing unit.

15 Claims, 5 Drawing Sheets

PORTABLE CORDLESS CARDIOPULMONARY ARREST RECORDER AND METHOD

BACKGROUND OF THE INVENTION

In the past there has been a need for recording the physiological data of a cardiopulmonary arrest patient. Such recording is desirable for the attending personnel whether it be in an emergency room of a hospital or otherwise. Such recording is used for entering data pertaining to the rhythm, medication and cardiovert/defibrillation to be analyzed in further treatment of the invention.

It is to be understood that such recording can take place in as varied a situation as can be imagined where time, readiness and simplicity in operation can be critical.

Various devices have been created for recording the physiological and ancillary data. Slavin U.S. Pat. No. 4,624,263 discloses a portable electrocardiograph which converts analog signals to digital with a processor and printer. The Ornato U.S. Pat. No. 4,457,312 records data during cardiac arrest on a flowsheet which is timed and taped. The Policastro U.S. Pat. No. 5,012,411 uses a portable self-contained processor for monitoring and storing physiological cardiac data and transmitting to a remote location with a printer.

While these patents show various features of recording data during a pulmonary cardiac arrest, and transmitting to a remote processing unit with a printer, there has remained a need for a simply employed portable cordless recorder for the patients rhythm, medication and cardiovert/defibrillation, timing significant events with means for adding additional data and viewing the data on a screen and physically transferring the unit or a self-contained computer disk capable of storing data associated with the recorder to a remote central processing unit for recording the data and recharging the unit.

SUMMARY OF THE INVENTION

By means of this invention, there has been provided a portable hand held cardiopulmonary arrest recorder which can be held by attending personnel to record the necessary data connected with the arrest.

The recorder is entirely self contained and is light weight and small size in order that it may be easily held by the physician or other attendant while monitoring the patient. It is cordless to provide maneuverability and freedom of encumbrances by electric cables or the like. Power is supplied by batteries, either replaceable or rechargeable at a remote central processing unit where the recorded data may be entered and printed out in a data sheet that may be transferred to the patient's bed side or to the patient's appropriate medical records as desired.

The portable recorder is designed to enter data in three main functions pertaining to the patient's rhythm, medication and cardiovert/defibrillation. A series of chronometers is also provided for entry of times for the particular data recorded. To provide adaptability for entry of data for the patient's condition, a keyboard for typing additional information is provided and a visual display screen to provide a sequential read out of events recorded.

The portable recorder in the three main sections has push button keys for recording the patient's data for rhythm, medication and cardiovert/defibrillation. In use, the recorder provides a simple, easy to use data recorder in recording the pertinent data regarding i.e. identified rhythm symptoms, medication, treatment and other observations. The recorder, after use, may be physically interfaced with the remote central processing unit for transfer of the recorded data, recharged and returned to standby for further use as required.

The above features are objects of this invention. Further objects will appear in the detailed description which follows and will be otherwise apparent to those skilled in the art.

For purpose of illustration of this invention a preferred embodiment is shown and described hereinbelow in the accompanying drawing. It is to be understood that this is for the purpose of example only and that the invention is not limited thereto.

IN THE DRAWINGS

DESCRIPTION OF THE INVENTION

Figure 1:
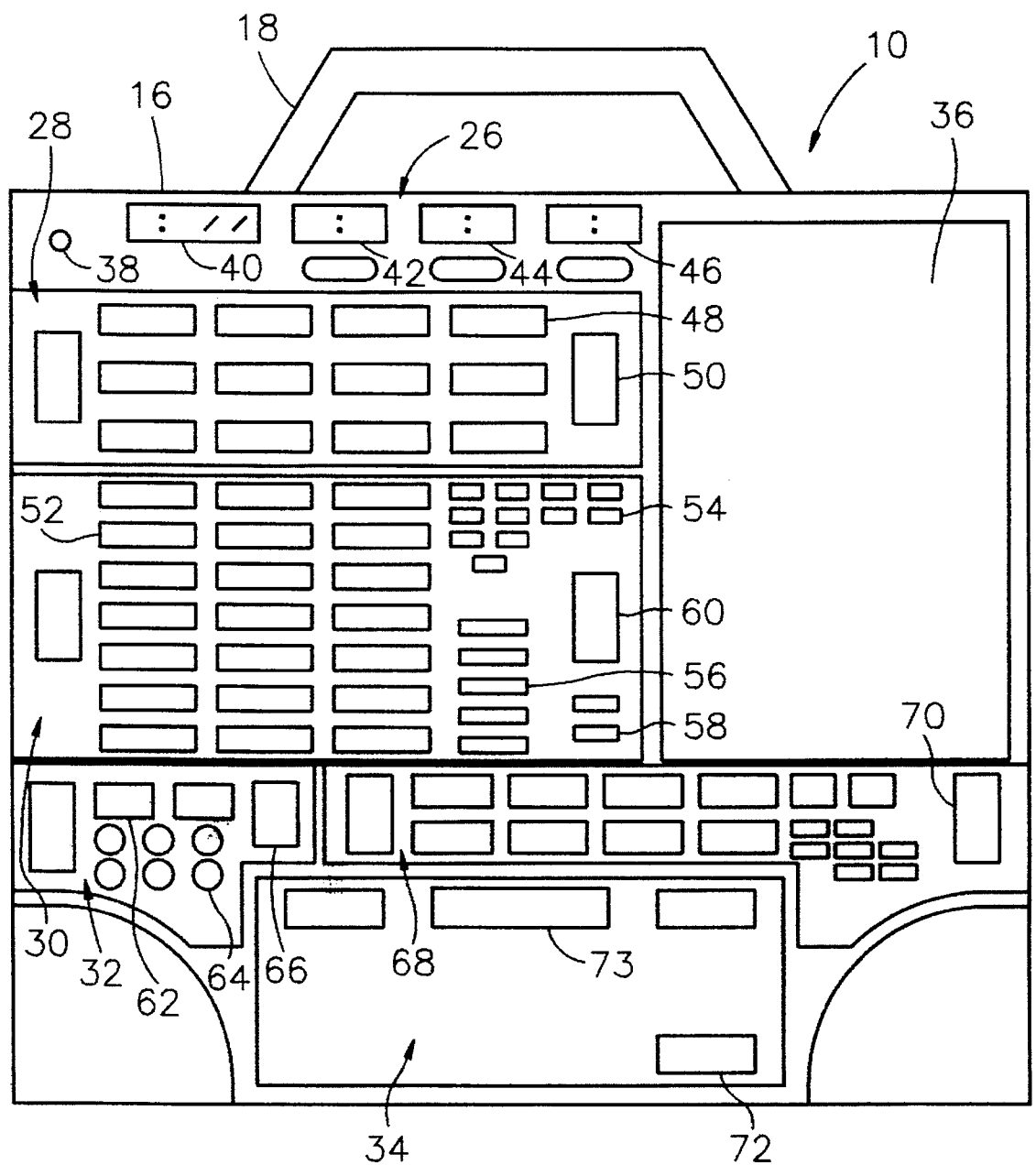
FIG. 1 is a view in front elevation of the cardiopulmonary arrest recorder.
Figure 1A:
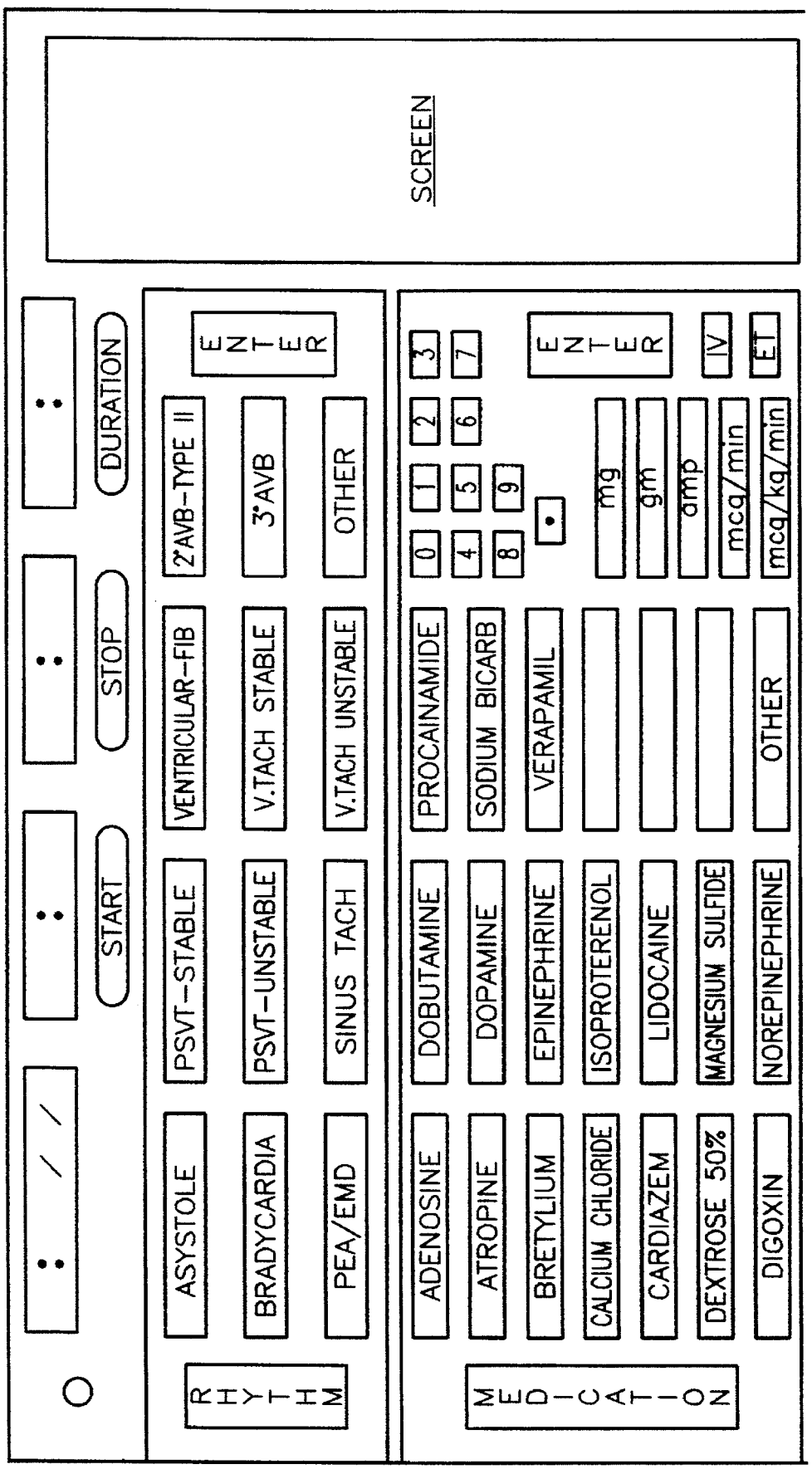
Figure 1B:
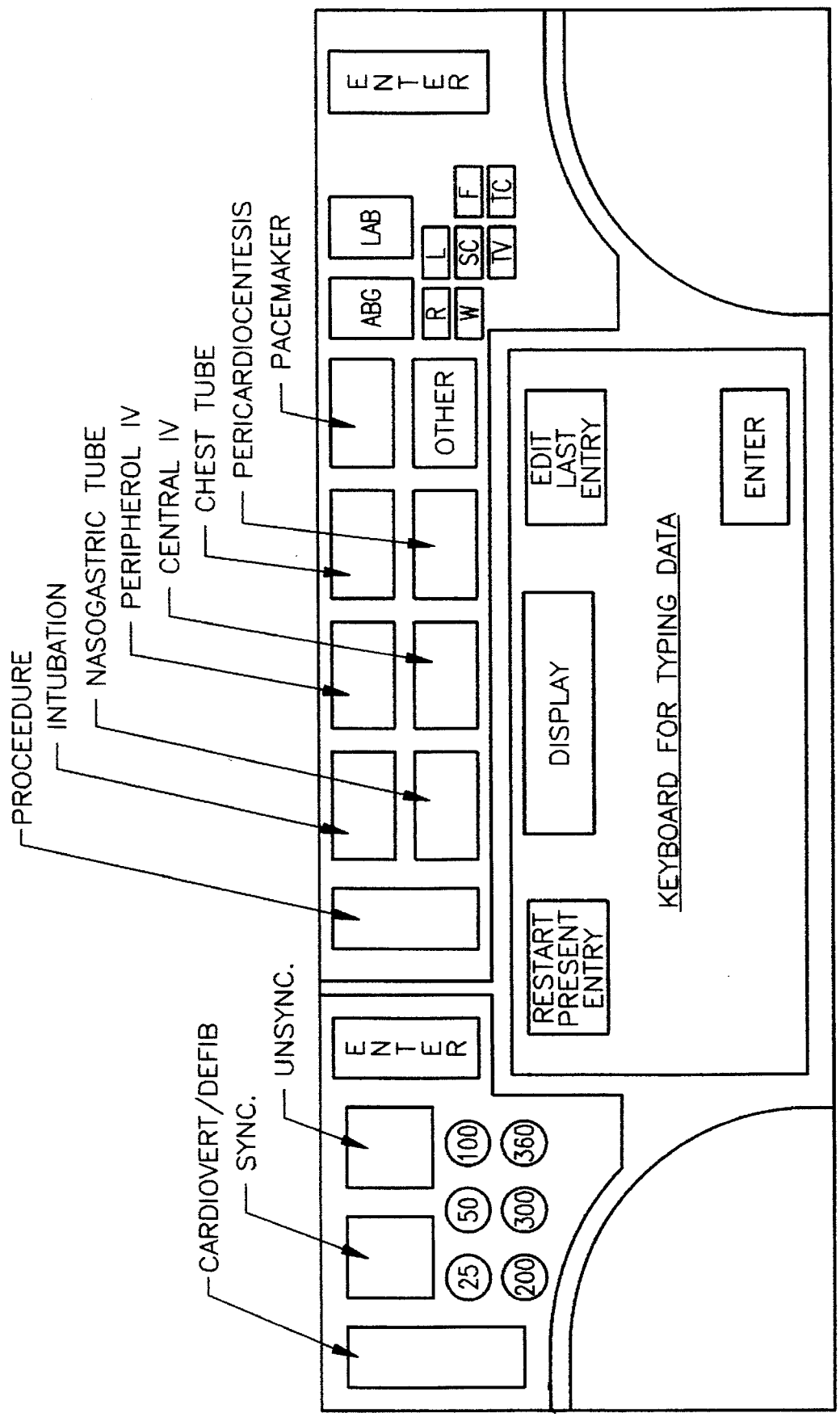
Figure 2:
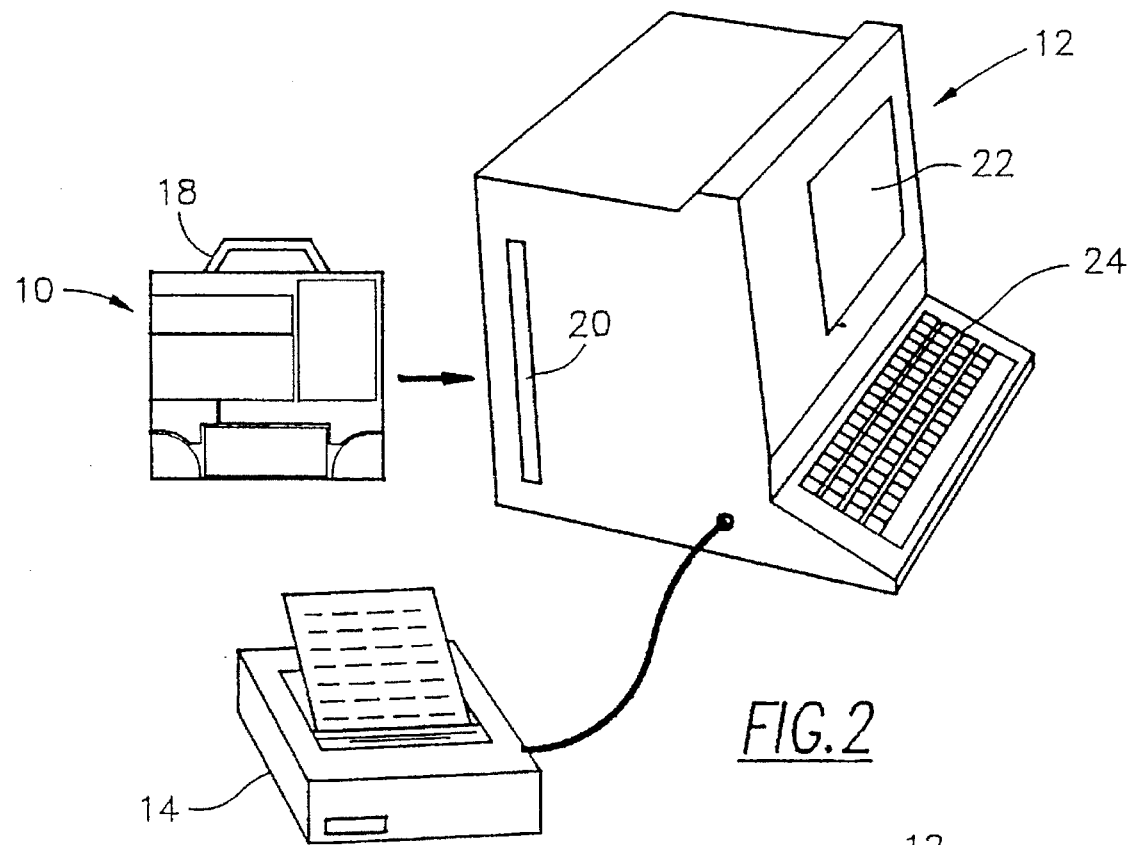
FIG. 2 is a pictorial view of the recorder in association with a central processing unit and printer.
Figure 3:
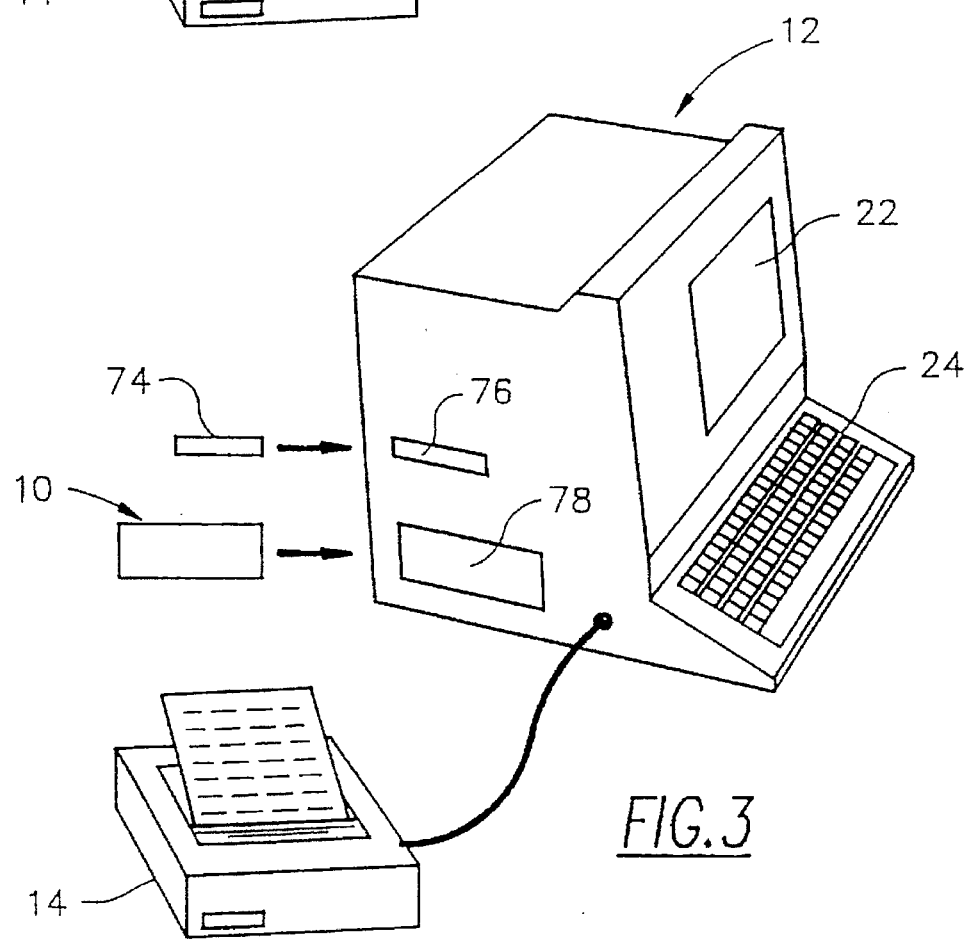
FIG. 3 is a pictorial view similar to FIG. 2 showing a modified use with a removable floppy disk or CD-ROM carried by the recorder.

The cardiopulmonary arrest recorder of this invention is generally indicated by the reference numeral 10 in FIGS. 1, 2 and 3. In FIGS. 2 and 3, it is shown ready for insertion and interfacing with a conventional central processing unit 12 additionally provided with a self contained battery charger and separate printer 14.

The recorder 10 is provided with a housing 16 having a handle 18 at the top for ease in carrying and a flexible handle (not shown) on a back panel. As an example, and without limitation, the housing may be approximately ten inches wide, eleven inches high and three-quarters of an inch deep with a weight of approximately two to three pounds.

For insertion and proper registry, grooves may be provided to slide along tracks in an opening 20 in the central processing unit or CPU 12. Charging of the battery within the recorder may be effected through a port in the bottom of the recorder which may be connected to a charging outlet or through a second port which may interface with a charger in the CPU.

The CPU 12 has a visual display screen 22, a series of keys 24 comprising engraved keys for various events and a standard keyboard with standard typing symbols. The CPU is provided with an internal program that allows for a predetermined step-by-step entry of data to the patient's cardiopulmonary arrest record. Once the data has been entered, it is available to the printer 14 to produce a copy of the event on a paper such as a pre-printed form that can be placed on the permanent chart.

The portable hand held recorder, since it is provided with a battery which may be recharged through a conventional recharger or the CPU 12, may be simply carried by the user to any desired location, be it an emergency room, or other area in a hospital or the field.

The recorder is provided with a number of important features which record the significant events in the treatment of a patient having a cardiopulmonary arrest. The main sections are a series of chronometers 26 for timing a series of events, a rhythm section 28 for physiological features of the patient, a medication section 30 pertaining to the prescribed medication, a cardiovert/defibrillation section 32 and a procedure section 68 for physical procedures to counter the cardiopulmonary arrest of the patient. A keyboard 34 is provided at the bottom of the panel for typing data not provided in the aforementioned sections while a display screen 36 serves as a visual indication of the entry of the data.

For further identification, the elements in the aforementioned sections will be described. In the chronometer section 26, a power on and off button 38 serves to energize the recorder. Chronometers 40, 42, 44 and 46 provide respectively, date and time, time of the event starting, stopping and duration. This provides a chronological history of the event.

In the rhythm section 28, a series of keys 48 provide a physiological analysis of the data entered by pressing one of the buttons, viewing the screen and depressing the enter button 50.

The medication section 30 has a series of keys 52 or buttons labeled with the names of standardly prescribed medicines, a dosage section 54, a prescribed dosage unit section 56, and a delivery section 58, intravenous or tracheal, along with an enter key 60.

The cardiovert/defibrillation section 32 has labeled keys 62 pertaining to synchronized and unsynchronized electrical shock with numbered keys 64 pertaining to energy level and an enter key 66. A section of keys 68 pertain to physical procedures with an enter key 70.

The keyboard 34 provides for entering of additional data for each of the sections and additional data as needed as editing and recording by enter key 72. A visual display section 73 is provided to illustrate data being entered from keyboards In FIG. 3, the recorder 10 is shown modified to be used with a physically transferrable magnetic media such as a computer disk capable of storing data 74. The disk may be a conventional floppy disk or a CD-ROM. In the latter case, a conventional WORM (Write Once Read Many) mechanism may be provided to create the CD-ROM. The recorder is constructed to receive the disk which may be removed from the recorder and inserted in opening 76 in the CPU for interfacing and transfer of data. Alternatively, the recorder with the disk may be inserted in opening 78 with or without the disk for transfer of data and recharging the battery of the recorder.

Figure 4:
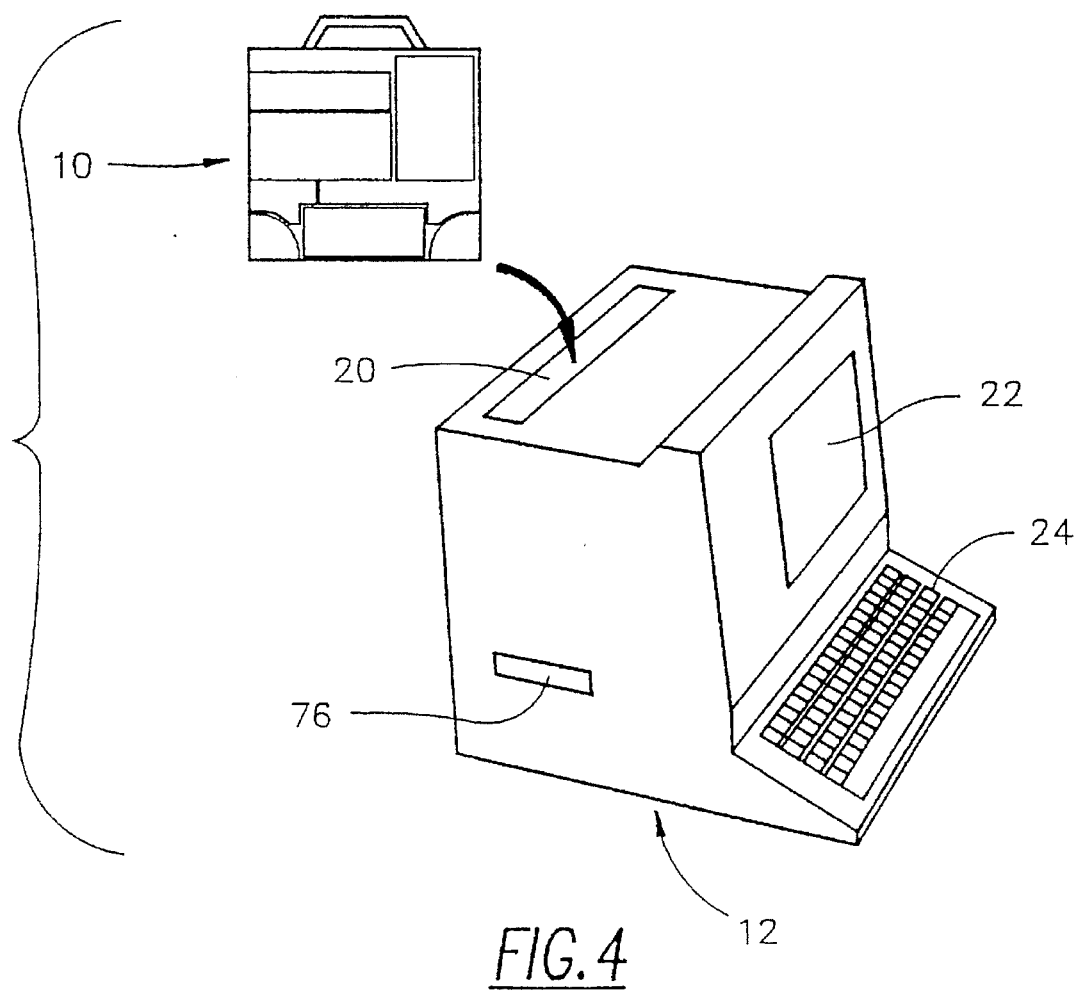
FIG. 4 is a pictorial view showing a further modified use of the recorder with the central processing unit.
Figure 5:
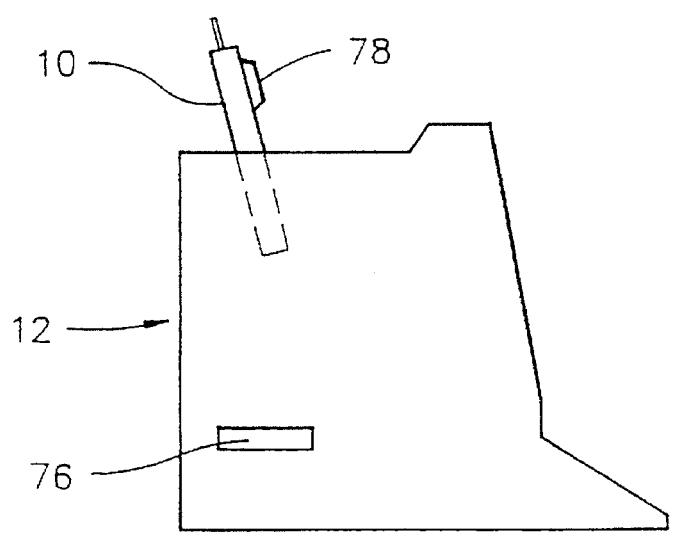
FIG. 5 is a view in right side elevation of the modified recorder and central processing unit.

A further modification of the system is shown in FIGS. 4 and 5. In this embodiment, the access slot 20 is shown at the top of the CPU 12 for easy "drop-in" of the recorder. The top handle 18 and rear handle 78 are both exposed for ready access. The access slot 76 has been moved to the right side of the CPU 12 for reception of the computer disk 74 where so provided for the recorder.

METHOD OF USE

The recorder 10 is very simply employed by the user responsible for recording data during a cardiopulmonary arrest procedure. Due to the light weight and compact nature, it lends itself to ease in use and is unobtrusive in the critical arena of the patient's treatment.

In use the recorder is first turned on and the significant times of treatment are recorded by the chronometers in section 26. The physiological features are observed and recorded in the rhythm section 28. The medication section 30 is used to provide a record of the medicine employed along with the dosage and manner of application. The cardiovert/defibrillation section 32 provides a record of any shock treatment as well as duration while various physical procedures may also be recorded in the procedure section 68.

The keyboard section 34 provides means for entering additional data not covered elsewhere along with means for editing by visual screen 16 and visual display 73 for clarity and ready reference.

After the treatment has been completed, the entire recorder may be transferred to the remote CPU 12 and physically interfaced by insertion in the slot 20. Transfer of data is effected and printout on printer 14 provides a visual record which may be placed in the patient's record or at his bedside for ready reference. Recharging of the recorder may be done in the CPU or by a separate recharging unit.

After transfer of data and any necessary recharging, the recorder is ready for further use. It will be understood that while the recorder is transferred to the remote location, other recorder may be made available as in a bank of recorders at the treatment site. Also, in the modified version of FIGS. 3–5 where a computer disk 74 is employed, the recorder may be kept at the treatment site while the disk is moved to the CPU 12 for transfer of the recorded data. The modification of FIGS. 4 and 5 further allows for the insertion of the recorder at the top of the CPU by "drop-in" or gravity for convenience in use. In this modification the handles are exposed for ready access.

Various changes and modifications may be made within this invention as will be apparent to those skilled in the art. Such changes and modifications are within the scope and teaching of this invention as defined in the claims appended hereto.

What is claimed is:

1. A system for recording cardiopulmonary arrest data comprising a portable hand held recorder having a self contained battery, chronometer means for timing significant events, said recorder having means physically engageable by a user for recording rhythm, medications, cardiovert/defibrillation data, and physical procedures in the recorder, a central processing unit said recorder comprising a housing and means for being physically interfacing said housing with said central processing unit for transferring the recorded data from said recorder, said means comprising receiving means in said processing unit physically engageable by said recorder housing in toto, said receiving means comprising a slot within which the recorder is deposited.

2. The system of claim 1 in which said recorder has a keyboard for typing in additional data and a visual screen for read out of the recorded data.

3. The system of claim 1 in which the recorder has a rechargeable battery means.

4. The system of claim 1 in which the recorder has a box-like housing and a hand grip at a top of the housing.

5. The system of claim 1 in which the recorder has a rechargeable battery means, a box-like housing and a hand grip at a top of the housing.

6. The system of claim 1 in which the recorder has a rechargeable battery means and is receivable with the recorder within a mounting means separate from the central processing unit.

7. The system of claim 1 in which a central processing unit is provided having a slot at a top of the unit which receives the recorder for interfacing and a hand grip at a top portion of the recorder exposed for ready access.

8. A system for recording cardiopulmonary arrest data comprising a portable hand held recorder having a self contained battery, chronometer means for timing significant events, said recorder having means physically engageable by a user for recording rhythm, medications, cardiovert/ defibrillation data, and physical procedures in the recorder, said recorder having means for being physically interfaced with a central processing unit for transferring the recorded data from said recorder, said means physically engageable by a user for recording rhythm, medication, cardiovert/ defibrillation, and physical procedures comprising a separate keyboard for each of said rhythm, medication, cardiovert/ defibrillation, and physical procedures with individual keys in each keyboard for recording designated usages.

9. A system for recording cardiopulmonary arrest data comprising a portable hand held recorder having a self contained battery, chronometer means for timing significant events, said recorder having means physically engageable by a user for recording rhythm, medications, cardiovert/ defibrillation data, and physical procedures in the recorder, said recorder having means for being physically interfaced with a central processing unit for transferring the recorded data from said recorder, said recorder having a keyboard for typing in additional data and a visual screen for read out of the recorded data, said means physically engageable by a user for recording rhythm, medication, cardiovert/ defibrillation, and physical procedures comprising a separate keyboard for each of said rhythm, medication, and cardiovert/defibrillation with individual keys in each keyboard for recording designated most generally employed usages.

10. A method for recording data associated with treatment of a cardiopulmonary arrest which comprises using a portable battery operated cordless hand held data recording, recording on said recorder significant time of events, physiological features in a rhythm section, recording medication data, cardiovert/defibrillation and procedure data, said recording being effected on a separate keyboard for each of said rhythm, medication, cardiovert/defibrillation, and physical producers with individual keys in each keyboard recording designated usages, observing said data on a visual screen and transferring the data from said recorder to a remote central processing unit by physically interfacing said recorder with said central processing unit.

11. The method of claim 10 in which the recorder is moved to said remote central processing unit and physically interfaced with it to transfer said data.

12. The method of claim 10 in which a keyboard on the recorder is operated to enter additional data.

13. The method of claim 10 in which the recorder battery is recharged in the central processing unit when transferred thereto.

14. The method of claim 10 in which the recorder is mounted for storage in a storing station and the battery is recharged therein.

15. The method of claim 10 in which the recorder is deposited for interfacing downwardly in the central processing unit within a slot in a top portion of a housing with a handle grip of the recorder exposed for ready access.

* * * * *